United States Patent [19]

Frensch et al.

[11] Patent Number: 4,571,088

[45] Date of Patent: Feb. 18, 1986

[54] PROCESS FOR THE PREPARATION OF DISPERSIONS OF PLANT PROTECTION AGENTS

[75] Inventors: Heinz Frensch, Frankfurt am Main; Konrad Albrecht, Kelkheim; Gerhard Frisch, Wehrheim, all of Fed. Rep. of Germany

[73] Assignee: Hoechst Aktiengesellschaft, Frankfurt, Fed. Rep. of Germany

[21] Appl. No.: 661,695

[22] Filed: Oct. 17, 1984

[30] Foreign Application Priority Data

Oct. 19, 1983 [DE] Fed. Rep. of Germany ....... 3337964

[51] Int. Cl.⁴ ............................................. B01F 15/00
[52] U.S. Cl. .................................... 366/136; 366/144; 366/176; 366/348
[58] Field of Search .................. 366/2, 101, 107, 144, 366/131, 132, 147, 148, 150, 159, 160, 161, 162, 167, 174, 176, 177, 136, 137, 348, 349

[56] References Cited

U.S. PATENT DOCUMENTS

| 3,254,045 | 5/1966 | Sinclair | 366/144 X |
| 3,676,075 | 7/1972 | Ploger et al. | 366/101 X |
| 3,738,815 | 6/1973 | Pawloski et al. | 366/148 X |
| 4,352,572 | 10/1982 | Chen et al. | 366/148 X |

Primary Examiner—Timothy F. Simone
Attorney, Agent, or Firm—Curtis, Morris & Safford

[57] ABSTRACT

The invention relates to a process for the preparation of dispersions of plant protection agents, wherein at least one active ingredient being metered, in the molten form, into the outlet stream of a jet, which stream contains a solution of the formulation aids. The process is suitable for all active ingredients which form a stable melt and have a melting point above 70° C. The resulting dispersions have advantageous stabilities.

12 Claims, 2 Drawing Figures

PROCESS FOR THE PREPARATION OF DISPERSIONS OF PLANT PROTECTION AGENTS

Dispersions of plant protection agents can be in the form of aqueous systems or alternatively, in rarer cases, in the form of oil dispersions. It is known to prepare dispersions of plant protection agents by wet grinding. In this process, the active ingredient is first precomminuted with the aid of so-called crushers and converted to powder form. The powdered active ingredient, together with the appropriate formulation aids, is then mixed in water or an organic solvent to give a premix. This premix is then ground by means of suitable wet grinding units to give the desired dispersions.

However, this process of preparation has the disadvantage of being very costly in terms of apparatus technology and being very energy-intensive. Boilers and mills of a very wide variety of types are required. In particular, the pulverizing, which affords an average particle size of ca. 2 $\mu$m or less, represents a very energy-intensive process.

Surprisingly, it has now been found that dispersions of plant protection agents can be prepared by metering at least one molten active ingredient into a turbulent stream, produced by means of a jet, of a solution of the formulation aids.

The present invention therefore relates to a process for the preparation of dispersions of plant protection agents which contain one or more active ingredients and customary formulation aids, wherein at least one active ingredient is metered, in the molten form, into the outlet stream of a jet, which stream contains an aqueous or organic solution of the formulation aids, and the temperature difference between the active ingredient melt and the solution of formulation aids being at least 150° C.

In principle, all active ingredients which do not decompose on melting are suitable. As regards the stability of the resulting dispersions, however, active ingredients with a melting point above 70° C. are particularly suitable since, in the case of active ingredients with a lower melting point, agglomerates can occasionally be formed if the product is exposed to elevated storage temperatures above the melting point of the active ingredient.

The process according to the invention makes it possible to prepare aqueous dispersions and oil dispersions. For the latter dispersions, the formulation aids are dissolved not in water but in high-boiling organic solvents such as white oils (long-chain paraffin oils), high-boiling aromatic solvents such as xylenes, methylnaphthalenes or the ®Solvesso types from ESSO, or high-boiling aliphatic or aromatic esters. The boiling point of these organic solvents should not be below 150° C. However, it is preferred to prepare water-based dispersions of plant protection agents by the process according to the invention.

The temperature difference between the active ingredient melt and the solution of formulation aids should preferably be more than 40° C. The upper limit of the temperature difference is determined by the melting point of the active ingredients used. In general, the active ingredient melts used are those whose temperature is only slightly above the melting point of the active ingredient, preferably 1° to 10° C. above the melting point. The temperature of the solution of formulation aids should appropriately be between 10° and 50° C.

Figure 1:
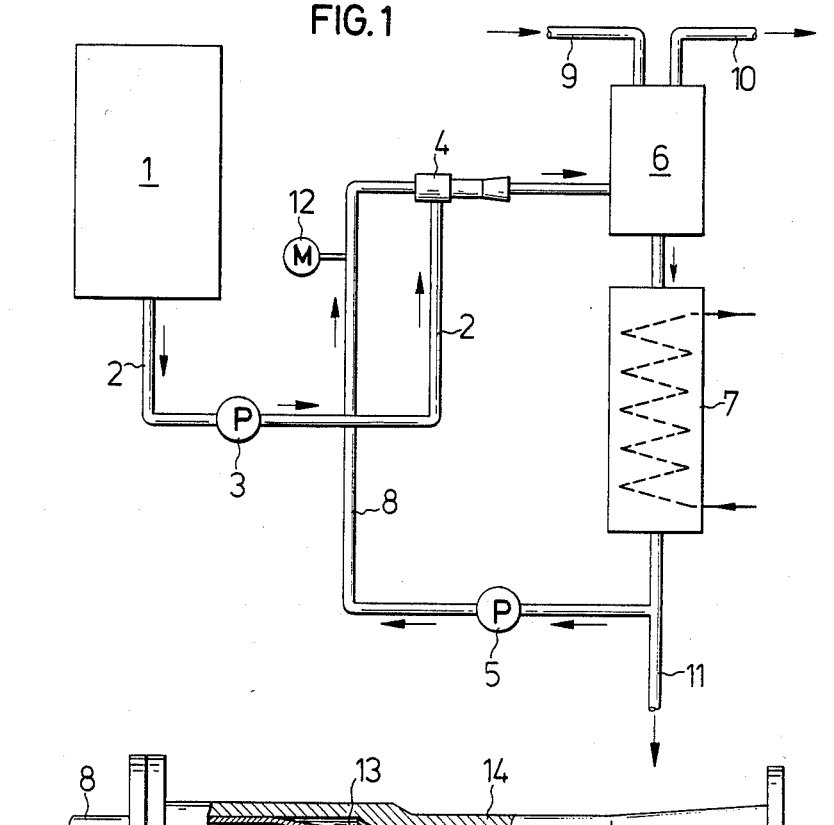
FIG. 1 is a schematic of the system according to the invention for carrying out the process.

The process according to the invention is advantageously carried out according to FIG. 1, in which the solution of formulation aids is circulated.

According to FIG. 1, the active ingredient is introduced in the molten state into a container (1). From the receiver (1), the active ingredient melt is conveyed to the jet (4) via a heated line (2) of the shortest possible length, by means of a suitable heatable pump (3), for example a piston pump, gear pump or centrifugal pump. This jet (4) is located in a circuit composed of a pump (5), a deflector (6) and an intensive cooling system (7). In this circuit, water or organic solvent, which contains the auxiliary substances required for the plant protection agent formulations, is circulated in the line (8) by means of the pump (5), for example a centrifugal pump or pressure piston pump. The auxiliary substances are introduced into the circuit via a line (9). A line (10) is used to ventilate the unit. The finished dispersion is removed from the circuit via a line (11).

The active ingredient melt is metered into this circuit via the jet (4). By means of the pump (5), a pressure of more than 0.3 bar is set up in the region between the pump (5) and the jet (4); pressures of between 3 bar and 40 bar are advantageous and pressures of between 4 and 35 bar are particularly preferred. The upper pressure limit is governed by the design of the unit. At a pressure above 40 bar, the cost of apparatus is too great. The pressure level is regulated by appropriate choice of the diameter of the line (8) and the choice of the jet (4) and also by the output of the pump (5), which can be adjustable. The jet (4) and the diameter of the line (8) are advantageously designed to have a constant relationship. The pressure is monitored by the manometer (12).

The mixture leaving the jet (4) is expanded in the deflector (6) and then led over the intensive cooling system (7) (heat exchanger) in order to keep the temperature of the circulation within a constant range. The suitable temperature of the circulated product varies with the type of active ingredient used; it is advantageously in the range between 10° and 50° C.

Figure 2:
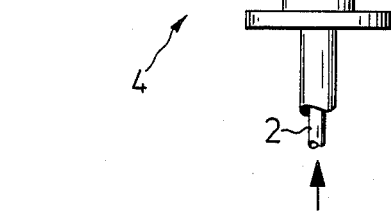
FIG. 2 is a sectional view of an example of the construction of a jet device.

The jet (4) to be used is shown diagrammatically in FIG. 2, it being possible to use any commercially available jets which correspond to the diagram of FIG. 2. The circulated aqueous solution enters the left-hand part of the jet under slight pressure and is accelerated more strongly through the jet restriction. At this stage, the ratio of the diameter of the inlet tube (8) to the diameter of the jet passage (13) (narrowest point of the jet) can vary in the range between 2:1 and 100:1, especially between 3:1 and 30:1. The data on the diameters of the devices according to FIGS. 1 and 2, given here and in the following text, all refer to internal diameters. The diameter of the inlet tube (8) for the circulated product is dependent on the flow rate of the circulation. The flow rate of the circulation is in turn in a particular ratio to the quantity of active ingredient metered in, this ratio being 1:1 to 500:1, preferably 1:1 to 100:1, particularly preferably between 5:1 and 50:1.

Underneath the jet restriction, the active ingredient is pumped as a melt through the heated inlet tube (2)

directly into the strongly turbulent outlet stream. The diameter of the exit of the inlet tube (8), namely the jet passage (13), can be between 2 and 30 mm, advantageously 4 to 10 mm, according to the design of the unit. In the outlet piece of the whole jet, namely in the jet exit (14), the melt is immediately micronized and quenched because of the high turbulences or shear forces present, this giving particles preferably having a diameter of 0.2 to 50 μm. The size of the particles can be regulated in particular via the pressure prevailing in the circuit: the higher the chosen pressure, the finer the resulting particles can become.

The receiver (1) of FIG. (1) represents any desired storage vessel containing the desired quantity of active ingredient. For some active ingredients, it can be advantageous to blanket the storage vessel with inert gas, for example nitrogen under a pressure of between 0.1 and 10 bar, in order to be able to meter the active ingredient into the circuit even better. In principle, it is possible to meter the active ingredient without the pump (3) and only with the aid of this inert gas pressure. The metering rate is variable and depends on the size of the unit.

The process according to the invention, described here as a batch process, can also be carried out continuously, the portion of the product removed from the circuit being replaced immediately, in a known manner, by metering in the corresponding quantity of starting materials. This can be regulated by known technical measuring and monitoring procedures.

Likewise, the process according to the invention makes it possible to prepare a dispersion with several active ingredients to be dispersed, by taking the appropriate active ingredients in the form of a mixture, converting this to a melt and metering it into the unit, or by connecting several storage vessels in parallel with the jet (4) or several jets.

With regard to the nature of the active ingredients, the process according to the invention is not limited to specific types. Thus, it is possible to use all known active ingredients of plant protection agents, such as, for example, fungicides, herbicides, insecticides and acaricides, which, as explained above, should have a melting point in particular above 70° C. This also applies to other substances which do not have a pesticidal activity but which can be processed to form dispersions.

Possible active ingredients are, in particular, sulfur, linuron, endosulfan, binapacryl, monolinuron, chlortoluron, isoproturon and diuron.

Likewise, it is also possible to use the customary auxiliary substances suitable for dispersions, such as the customary wetting and dispersing agents, emulsifiers, thickeners and antifoams.

See, for example, Sandoz brochure 9151/82 Surfactants for Pesticides, Soprosoie brochure (1981/82) from Rhône Poulenc, Dehydag brochure Raw Materials for the Chemical Engineering Industry, 2nd edition (1982) from Henkel, and Atlas-Surfactants brochure EC-G34-80 from Atlas Chemie.

The invention is illustrated in greater detail by means of the examples which follow.

EXAMPLES 1 to 6

The apparatus shown in FIG. 1 was used with the jet according to FIG. 2. The jet inlet tube (8) for the aqueous solution had a diameter of 14 mm and the inlet tube (2) for the active ingredient melt had a diameter of 4 mm. The jet passage (13) had a diameter of 4.5 mm and the jet exit (14) had a diameter of 10 mm. The ratio of the flow rate in circulation to the quantity of active ingredient melt metered in was regulated by the metering rate of the active ingredient melt, given below, at the corresponding adjusted pressure in the circulation (given below). The temperature of the circulation varied between 20° and 50° C. The temperature of the active ingredient melt is given in the examples.

EXAMPLE 1

Active ingredient: 3.5 kg of endosulfan (technical grade) with a temperature of 95° C.
Auxiliary substances: 0.7 kg, consisting of the Na salt of sulfosuccinic acid half-ester (0.4 kg), alumosilicate (®Darvan No. 3) (0.05 kg), ethylene glycol (0.2 kg) and silicone antifoam SE2 (0.05 kg)
Water: 5.8 kg
Pressure in the circulation: 4 bar
Metering rate of the active ingredient: 7.2 kg/hour.

A stable dispersion with an average particle size of 1.5μ was obtained.

EXAMPLE 2

The same composition and temperature as in Example 1 were chosen. At a pressure of 10 bar in the circulation and a metering rate of 9 kg/hour, a stable dispersion with a particle size of 1.2μ was obtained.

EXAMPLE 3

Active ingredient: 4.0 kg of linuron (technical-grade) with a temperature of 90° C.
Auxiliary substances: 0.6 kg, consisting of ligninsulfonate (0.45 kg), alumosilicate (®Darvan No. 3) (0.1 kg) and silicone anti-foam (0.05 kg)
Water: 5.4 kg
Pressure in the circulation: 7 bar
Metering rate of the active ingredient: 12 kg/hour.

A stable dispersion with a particle size of 1.6μ was obtained.

EXAMPLE 4

Active ingredient: 3.0 kg of linuron (technical-grade), temperature: 90° C.
Auxiliary substances: 0.75 kg, consisting of 0.1 kg of ®Darvan No. 3, 0.4 kg of ligninsulfonate, 0.2 kg of the Na salt of sulfosuccinic acid half-ester and 0.05 kg of silicone antifoam
Water: 6.25 kg
Pressure in the circulation: 25 bar
Metering rate of the active ingredient: 2 kg/hour.

A stable dispersion with an average particle size of 1.1μ was obtained.

EXAMPLE 5

Active ingredient: 5 kg of sulfur, temperature: 120° C.
Auxiliary substances: 0.5 kg, consisting of 0.25 kg of ligninsulfonate, 0.2 kg of nonylphenol ethoxylated with 30 EO and 0.05 kg of alumosilicate (®Darvan No. 3)
Water: 4.5 kg
Pressure in the circulation: 6 bar
Metering rate: 5 kg/hour.

A stable dispersion with an average particle size of 1.6μ was obtained.

EXAMPLE 6

Active ingredient: 12.0 kg of sulfur, temperature: 120° C.

Auxiliary substances: 2.7 kg, consisting of 1.35 kg of ligninsulfonate, 0.9 kg of nonylphenol ethoxylated with 30 EO, 0.3 kg of antifoam and 0.15 kg of ®Darvan No. 3

Water: 15.3 kg

Pressure in the circulation: 8 bar

Metering rate: 6 kg/hour.

A stable dispersion with an average particle size of 1.5μ was obtained.

What is claimed is:

1. A process for the preparation of dispersions of plant protection agents which contain one or more active ingredients and auxiliary formulation aids, wherein at least one active ingredient is metered, in molten form, into an outlet stream of a jet, which outlet stream contains an aqueous or organic solution of the formulation aids, and the temperature difference between the molten active ingredient and the solution of formulation aids being at least 15° C.

2. The process as claimed in claim 1, wherein active ingredients with a melting point above 70° C. are used.

3. The process as claimed in claim 1, wherein the temperature difference between the molten active ingredient and the solution of formulation aids is more than 40° C.

4. The process as claimed in claim 1, wherein the temperature of the solution of formulation aids is between 10° and 50° C.

5. The process as claimed in claim 1, wherein the temperature of the molten active ingredient is 1° to 10° C. above the melting point of the active ingredient.

6. The process as claimed in claim 1, wherein the solution of formulation aids is circulated.

7. The process as claimed in claim 1, wherein the molten active ingredient is metered into the jet under a pressure of 0.1 to 10 bar.

8. The process as claimed in claim 1, wherein the ratio of the diameter of a jet inlet tube through which the solution of formulation aids is introduced, to the diameter of the narrowest portion of a passage through the jet, varies in the range between 2:1 and 100:1.

9. The process as claimed in claim 1, wherein the solution of formulation aids is pumped into the jet under a pressure of between 3 and 40 bar.

10. A process for the preparation of a dispersion of a plant protection agent which contains an active ingredient and auxiliary formulation aids comprising metering at least one molten active ingredient of a plant proection agent into a turbulent stream containing an aqueous or organic solution of the auxiliary formulation aids and the temperature difference between the molten active ingredient and the solution of the formulation aids being at least 15° C.

11. The process, as claimed in claim 10, wherein the active ingredient has a melting point above 70° C.; the temperature difference between the molten active ingredient and the solution of auxiliary formulation aids is more than 40° C.; and the temperature of the molten active ingredient is 1° to 10° C. above the melting point of the active ingredient.

12. The process, as claimed in claim 11, wherein the molten active ingredient is metered into an outlet stream of a jet having an inlet tube and an opening defining a passage through the jet, said outlet stream containing the solution of auxiliary formulation aids and the ratio of the diameter of the inlet tube to the diameter of the narrowest portion of the opening being in the range between 3:1 and 30:1.

* * * * *